United States Patent [19]

Kuranda

[11] Patent Number: 5,258,502
[45] Date of Patent: Nov. 2, 1993

[54] IMMOBILIZATION AND PURIFICATION OF FUSION PROTEINS USING CHITIN-BINDING ABILITY

[75] Inventor: Michael J. Kuranda, Acton, Mass.

[73] Assignee: Massachusetts Institute of Technology, Cambridge, Mass.

[21] Appl. No.: 303,827

[22] Filed: Jan. 30, 1989

[51] Int. Cl.⁵ .................. C07K 3/18; C07K 15/04; C12P 21/00; C12N 15/56
[52] U.S. Cl. .................... 530/350; 530/413; 435/69.7; 435/320.1; 435/254.21; 536/23.4; 536/23.74; 935/69
[58] Field of Search .................... 435/69.1, 69.7, 69.9, 435/71.1, 172.3, 320.1; 935/28, 47, 48, 69; 536/27; 530/350, 413

[56] References Cited

U.S. PATENT DOCUMENTS 4,615,974 10/1986 Kingsman et al. ............... 435/69.51
4,751,081 6/1988 Suslow et al. .................... 424/93

FOREIGN PATENT DOCUMENTS 290123 9/1988 European Pat. Off. .

OTHER PUBLICATIONS

Moks, et al. Expression of Human Insulin-like Growth Factor I in Bacteria: Use of Optimized Gene Fusion Vectors... Biochemistry vol. 26, No. 17, pp. 5239-5244 1987.
Kuranda, et al. Cloning and Heterologous Expression of Glycosidase Genes From Saccharomyces Cerevisiae Proc. Natl. Acad. Sci. USA vol. 84, pp. 2585-2589 1987.
Correa, et al. Endochitinase, A Mannan-Associated Enzyme From Saccharomyces Cerevisiae J. Biol. Chemistry vol. 257, No. 4, pp. 1392-1397 1982.

Kuranda, J. J. & P. Robbins, *Proceedings of the National Academey of Sciences*, USA, 84: 2585-2589, (May 1987).
Robbins, P. W. et al., *Journal of Biological Chemistry*, 263(1): 443-447 (Jan. 5, 1988).
Harpster, M. H. et al., *Mol. Gen. Genet.*, 212:182-190, (1988).
Jones, J. D. G. et al., *Mol. Geb. Genet.*, 212:536-542 (1988).
Taylor, J. L. et al., *Mol. Gen. Genet.*, 210:572-577 (1987).
Correa, J. U. et al., *Journal of Biological Chemistry*, 257(3):1392-1397 (1982).
Greenwood, J. M. et al., *FEBS Letters*, 244(1):127-131 (1989).
Ong, E. et al., *Biotechnology*, 7:604-607 (1989).

*Primary Examiner*—David L. Lacey
*Assistant Examiner*—George C. Elliott
*Attorney, Agent, or Firm*—Hamilton, Brook, Smith & Reynolds

[57] ABSTRACT

A gene fusion construction encoding a protein of interest and the chitin binding domain of a chitinase enzyme and the encoded fusion protein, which is the protein of interest and a protein capable of binding chitin. A plasmid vector containing the gene fusion construction is also described. The vector is used to transform host cells, which produce and secrete the recombinant fusion protein.

The fusion protein is isolated by binding to chitin through its chitin-binding domain. The present method uses chitin to bind the fusion protein through its chitin-binding domain, and thereby allows immobilization and/or purification of the protein of interest, using known techniques.

28 Claims, 10 Drawing Sheets

| | amino acids |
|---|---|
| A - Signal sequence | 1-20 |
| B - Hydrolytic Region | 21-308 |
| C - Ser, Thr Rich Region | 309-480 |
| D - Chitin Binding Domain | 481-562 |

Fig. 2A

DNA SEQUENCE OF CTS2

```
      BglII
      AGATCTTTCACTCATTTAAGACTCAATAACATAAAAAAAATAAACCTGTCATTCCTTTGA
  1   ---------+---------+---------+---------+---------+---------+   60

ACCTTTTTATATCCAAAAATAATAACTGTCGCTCGTTTCACAACCTACCTTTTTTAAAAC
 61   ---------+---------+---------+---------+---------+---------+  120

CACTCTTTTTCCAATACATTGAAATTCTAATTTAAATATAAAATAATTAATAATAGAATG
121   ---------+---------+---------+---------+---------+---------+  180
                                                                 M signal sequence
      TCACTCCTTTACATCATTCTTCTATTCACACAATTCTTACTACTGCCAACCGATGCCTTT
181   ---------+---------+---------+---------+---------+---------+  240
       S  L  L  Y  I  I  L  L  F  T  Q  F  L  L  L  P  T  D  A  F hydrolytic region
      GATAGGTCTGCTAACACAAATATTGCTGTTTATTGGGGTCAAAACTCAGCAGGAACGCAA
241   ---------+---------+---------+---------+---------+---------+  300
       D  R  S  A  N  T  N  I  A  V  Y  W  G  Q  N  S  A  G  T  Q GAATCCTTAGCTACTTACTGTGAATCTTCTGATGCTGATATTTTCCTATTATCTTTCTTG
301   ---------+---------+---------+---------+---------+---------+  360
       E  S  L  A  T  Y  C  E  S  S  D  A  D  I  F  L  L  S  F  L AACCAATTTCCAACCCTTGGTTTGAACTTTGCCAACGCATGCTCTGATACTTTTTCTGAT
361   ---------+---------+---------+---------+---------+---------+  420
       N  Q  F  P  T  L  G  L  N  F  A  N  A  C  S  D  T  F  S  D GGCTTACTTCACTGCACCCAGATTGCTGAAGATATTGAAACTTGCCAGTCCCTAGGAAAG
421   ---------+---------+---------+---------+---------+---------+  480
       G  L  L  H  C  T  Q  I  A  E  D  I  E  T  C  Q  S  L  G  K AAAGTTCTATTATCATTAGGTGGTGCATCTGGTAGCTACCTCTTTTCAGATGATTCTCAA
481   ---------+---------+---------+---------+---------+---------+  540
       K  V  L  L  S  L  G  G  A  S  G  S  Y  L  F  S  D  D  S  Q GCGGAAACTTTTGCACAAACTTTATGGGATACTTTCGGTGAAGGTACAGGTGCCAGTGAG
541   ---------+---------+---------+---------+---------+---------+  600
       A  E  T  F  A  Q  T  L  W  D  T  F  G  E  G  T  G  A  S  E
```

Fig. 2B

```
         AGACCATTTGACTCAGCAGTCGTTGATGGTTTTGATTTTGATATTGAAAACAACAACGAA
601      ------------+---------+---------+---------+---------+---------+  660
         R  P  F  D  S  A  V  V  D  G  F  D  F  D  I  E  N  N  N  E

GTAGGCTATAGTGCGTTACGTACCAAGTTAAGAACTTTGTTTGCCGAAGGTACAAAGCAA
661      ------------+---------+---------+---------+---------+---------+  720
         V  G  Y  S  A  L  R  T  K  L  R  T  L  F  A  E  G  T  K  Q

TATTACCTTTCTGCCGCACCACAATGTCCATACCCGGATGCTTCTGTTGGTGACTTGTTG
721      ------------+---------+---------+---------+---------+---------+  780
         Y  Y  L  S  A  A  P  Q  C  P  Y  P  D  A  S  V  G  D  L  L

GAAAATGCAGACATTGATTTTGCGTTCATCCAATTTTACAATAATTACTGCAGTGTGAGT
781      ------------+---------+---------+---------+---------+---------+  840
         E  N  A  D  I  D  F  A  F  I  Q  F  Y  N  N  Y  C  S  V  S

GGTCAATTCAATTGGGATACTTGGTTAACCTATGCTCAAACTGTATCCCCAAATAAAAAT
841      ------------+---------+---------+---------+---------+---------+  900
         G  Q  F  N  W  D  T  W  L  T  Y  A  Q  T  V  S  P  N  K  N

ATCAAACTGTTCTTAGGTTTACCTGGTTCTGCTTCTGCTGCTGGCTCTGGTTATATTTCT
901      ------------+---------+---------+---------+---------+---------+  960
         I  K  L  F  L  G  L  P  G  S  A  S  A  A  G  S  G  Y  I  S

GACACTTCTTTATTGGAATCAACTATTGCAGATATTGCCTCTTCAAGTTCTTTTGGTGGT
961      ------------+---------+---------+---------+---------+---------+  1020
         D  T  S  L  L  E  S  T  I  A  D  I  A  S  S  S  S  F  G  G

ATTGCGTTATGGGATGCATCTCAAGCCTTTTCCAACGAGCTAAATGGTGAACCATATGTT
1021     ------------+---------+---------+---------+---------+---------+  1080
         I  A  L  W  D  A  S  Q  A  F  S  N  E  L  N  G  E  P  Y  V hydrolytic region ———→|←——— ser,thr rich region
         GAGATTTTGAAGAATTTGCTAACAAGTGCTAGCCAGACCGCCACTACTACAGTTGCCACC
1081     ------------+---------+---------+---------+---------+---------+  1140
         E  I  L  K  N  L  L  T  S  A  S  Q  T  A  T  T  T  V  A  T TCAAAAACCTCAGCAGCCTCAACTTCATCTGCTTCAACTTCATCTGCTTCAACTTCTCAG
1141     ------------+---------+---------+---------+---------+---------+  1200
         S  K  T  S  A  A  S  T  S  S  A  S  T  S  S  A  S  T  S  Q AAAAAGACCACACAATCTACGACATCTACACAAAGTAAAAGCAAAGTTACTTTATCTCCA
1201     ------------+---------+---------+---------+---------+---------+  1260
         K  K  T  T  Q  S  T  T  S  T  Q  S  K  S  K  V  T  L  S  P
```

Fig. 2C

```
     ACTGCAAGCAGCGCTATCAAAACATCAATTACTCAAACTACAAAAACATTGACGAGTAGC
1261 ---------+---------+---------+---------+---------+---------+ 1320
     T  A  S  S  A  I  K  T  S  I  T  Q  T  T  K  T  L  T  S  S

ACCAAGACAAAATCTAGTCTAGGTACCACCACAACAGAGAGCACTTTAAATTCAGTTGCT
1321 ---------+---------+---------+---------+---------+---------+ 1380
     T  K  T  K  S  S  L  G  T  T  T  T  E  S  T  L  N  S  V  A

ATCACAAGTATGAAAACTACTCTATCTTCCCAAATAACCAGTGCTGCCTTGGTGACCCCT
1381 ---------+---------+---------+---------+---------+---------+ 1440
     I  T  S  M  K  T  T  L  S  S  Q  I  T  S  A  A  L  V  T  P

CAAACAACTACTACTAGCATAGTTTCTTCGGCCCCAATTCAAACAGCTATCACTAGTACT
1441 ---------+---------+---------+---------+---------+---------+ 1500
     Q  T  T  T  T  S  I  V  S  S  A  P  I  Q  T  A  I  T  S  T

CTTTCGCCAGCAACGAAGAGTTCTTCTGTCGTTTCCCTACAGACAGCTACTACTAGTACG
1501 ---------+---------+---------+---------+---------+---------+ 1560
     L  S  P  A  T  K  S  S  S  V  V  S  L  Q  T  A  T  T  S  T ser, thr rich region             ───────►│◄──
     CTTTCCCCAACAACGACCAGTACAAGCTCAGGTAGTACAAGCTCAGGTAGTACAAGCTCA
1561 ---------+---------+---------+---------+---------+---------+ 1620
     L  S  P  T  T  T  S  T  S  S  G  S  T  S  S  G  S  T  S  S chitin binding domain
     GACAGTACAGCTCGTACATTGGCTAAAGAATTGAATGCTCAATATGCGGCTGGTAAATTG
1621 ---------+---------+---------+---------+---------+---------+ 1680
     D  S  T  A  R  T  L  A  K  E  L  N  A  Q  Y  A  A  G  K  L AACGGTAAATCTACCTGTACTGAAGGTGAAATTGCATGCTCTGCTGATGGGAAGTTCGCC
1681 ---------+---------+---------+---------+---------+---------+ 1740
     N  G  K  S  T  C  T  E  G  E  I  A  C  S  A  D  G  K  F  A GTTTGTGATCATAGCGCTTGGGTTTACATGGAATGTGCTTCTGGAACCACATGTTATGCT
1741 ---------+---------+---------+---------+---------+---------+ 1800
     V  C  D  H  S  A  W  V  Y  M  E  C  A  S  G  T  T  C  Y  A TATGACTCCGGCGACTCAGTCTATACCCAATGTAATTTCTCTTATTTGGAAAGCAATTAC
1801 ---------+---------+---------+---------+---------+---------+ 1860
     Y  D  S  G  D  S  V  Y  T  Q  C  N  F  S  Y  L  E  S  N  Y TTTTAAAGTTATTAGAGATTGATTCATAGAGTCCGAATATTTTTTTTGCAATATTCTTT
1861 ---------+---------+---------+---------+---------+---------+ 1920
     F  *
```

Fig. 2D

```
         ATTTTTCACCTCATCTCACCGCCTCTCTTTTATTTCGTCAAGGTACCCTGCCTTCATGTT
1921     ---------+---------+---------+---------+---------+---------+ 1980

TTTACGTTTTTATAATCGACTACTTTATATCTATAACGAATTATTTAATTTTCTTCGATT
1981     ---------+---------+---------+---------+---------+---------+ 2040

EcoRI
         TACTGTGTTTCTACCATTTTGCGAATTCGTGCCCCATCATGACTTATTTTATTTAATTGT
2041     ---------+---------+---------+---------+---------+---------+ 2100

TACATATCAAAGGACACTGGTTTACAAACATAAAAATGATTGTTGAGAATGCCAATTCCG
2101     ---------+---------+---------+---------+---------+---------+ 2160

CACTCCCACTTACTACTTTTCATGTGTTAAATAGTACGCATAAACACGAGATCT
2161     ---------+---------+---------+---------+---------+---- 2214
```

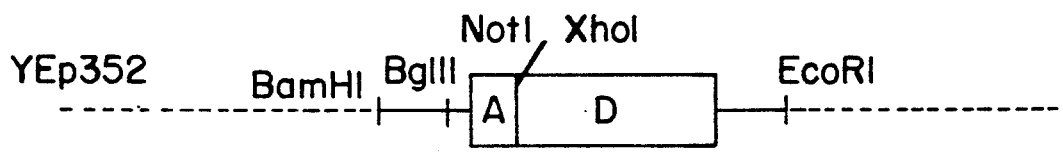
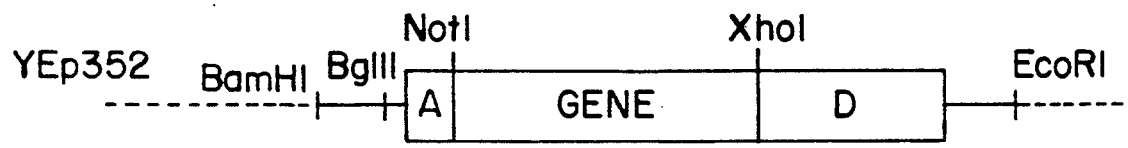
FIG. 3.

IMMOBILIZATION AND PURIFICATION OF FUSION PROTEINS USING CHITIN-BINDING ABILITY

GOVERNMENT SUPPORT

Work described herein was supported by funding from the National Institutes of Health.

BACKGROUND

The cell wall of *Saccharomyces cerevisiae* (*S. cerevisiae*) is composed of a series of widely studied polysaccharides. Glucan, a major component, is a glucose homopolymer consisting of repeating (1-3)beta-D residues. In addition to structural glucans, the cell wall contains roughly equal amounts of "mannan", a mannose-containing polymer. Chitin, a (1-4)-beta-D-linked polymer of N-acetylglucosamine, comprises only about 1% of the total cell wall. This minor component has drawn interest due to its localized deposition in the septa of budding cells.

The rigid architecture of the wall, which dictates the characteristic shape of the cell, must accommodate changes in morphology that accompany processes such as budding, sporulation, or "shmoo" formation. Structural alterations essential to these processes may be accomplished in part through the regulated catabolism of the cell wall. Consistent with this hypothesis, a number of autolytic hydrolases have been reported to be associated with the yeast cell envelope, including several exo- and endoglucanases and an endochitinase activity. Additionally, α-mannosidase activities capable of hydrolyzing mannose oligosaccharides or p-nitrophenyl-α-D-mannopyranoside have been found in *S. cerevisiae*.

A large number of human and other proteins have been produced in host cells by transfecting these cells with DNA encoding these proteins and growing the recombinant cells under conditions favorable for the expression of the protein. In some cases, the proteins are secreted by the cells into the cell culture medium, and must be separated from the culture medium and the other components, such as cell waste products, cell debris and proteins or other material, which also has collected in the medium. To be useful, the biological activity of the protein must be preserved. Thus, recovery conditions must be mild enough to preserve the biological activity of the protein, but, at the same time, suitable for effective separation of the protein from contaminants in the medium. Purity is often an important consideration, especially for pharmaceutical application.

Recovery of proteins in biologically active form from cell culture medium presents a number of problems. For example, the desired protein must be separated from other closely related proteins in the cell culture medium, such as homologous, biologically inactive proteins, which may be associated with the protein. Further, the desired protein must generally be recovered in such a way that it retains its native activity. Preferably, the process used should result in recovery of the biologically active form of the protein with a high level of purity.

SUMMARY OF THE INVENTION

The present invention relates to a nucleotide sequence which encodes a product capable of binding to chitin (referred to as a nucleotide sequence encoding a chitin-binding product); to a gene fusion construction which includes a nucleotide sequence encoding a chitin-binding product and a gene of interest (i.e., a nucleotide sequence encoding a protein of interest, which is a protein or polypeptide to be immobilized or purified by the present method); and to the recombinant product encoded by such gene fusion constructs. It also relates to a method of immobilizing and purifying a Protein, or a portion thereof, (e.g., polypeptide, oligopeptide) which is produced in an appropriate host cell as a component of a recombinant protein which has the ability to bind chitin.

In particular, the present invention relates to gene fusion constructions comprising: a) all or a portion of the noncatalytic chitin-binding domain of the *S. cerevisiae* endochitinase gene, encoding a product capable of binding chitin; b) a nucleotide sequence (DNA) encoding a protein of interest; and, optionally c) other nucleotide sequences such as those encoding the yeast endochitinase signal sequence (or other signal sequence) and/or the yeast endochitinase promoter (or other promoter), useful in expression of the encoded recombinant product and its secretion from the host cell in which the recombinant product is made. It further relates to recombinant products, referred to as fusion proteins, which include a chitin-binding component and a protein of interest. It also relates to a method of immobilizing and/or purifying a protein of interest by imparting to or conferring upon the protein the ability to bind chitin (through addition to the protein of interest of a chitin-binding component, resulting in production of a fusion protein) and contacting the protein of interest with chitin, under conditions appropriate for binding of the chitin-binding component of the fusion protein and the chitin to occur. Once bound to the chitin, the fusion protein can be isolated or purified and, if desired, the protein of interest separated from the chitin-binding component, using known techniques.

The presence in the fusion protein of the chitinase chitin binding domain allows the recombinant protein to be isolated from the cell culture medium by binding to chitin. The chitin-bound protein can then be released from the chitin substrate, and the protein of interest can be cleaved from the peptide sequence representing the chitin binding domain, yielding isolated, pure protein.

The method of the invention provides a procedure by which fusion protein, produced by a transformed host cell after transfection of the cell with the DNA encoding the protein, is recovered and purified.

The present process is an efficient, non-denaturing process for recovering substantially pure, biologically active protein.

The production of chitin binding domain fusions with a gene of interest offers a general approach for the rapid purification of the corresponding protein on a laboratory or industrial scale. Chitin, the adsorption matrix, can be readily obtained inexpensively in large quantities and in high purity. Chitin is inert under physiological conditions and it is unlikely to interfere with reactions catalyzed by bound fusions. In addition, chitin is nonimmunogenic and therefore will not generate an immune response if present in trace amounts in preparations used in vivo.

This system can be easily adapted to a variety of commercially important expression vectors. A segment of a chitinase gene containing the chitin binding domain, which has been expressed in yeast and in bacterial cells, such as *E. coli*, retains its chitin binding properties. Proteins can also be expressed in mammalian cells using a vector suitable for expression in mammalian cell culture.

The present invention results in a rapid and inexpensive way to immobilize recombinant proteins, and provides a useful method for the isolation and purification of recombinant proteins from a culture medium or other solution.

BRIEF DESCRIPTION OF THE FIGURES

FIGS. 2A-2D show the nucleotide sequence and corresponding amino acid sequence (using the single letter code for amino acids) of the *Saccharomyces cerevisiae* endochitinase gene, CTS2. The restriction sites (BgIII and EcoRI) indicated are the same as those represented in FIG. 1. The locations of the signal sequence; the hydrolytic region; the serine, threonine rich region and the chitin binding domain are indicated.

FIG. 3 is a schematic representation of the expression vector pCT32 and of the same vector with a gene of interest inserted into the NotI-XhoI junction.

FIG. 6A shows restriction sites on CTS1 and FIG. 6B shows the site of insertion of the auxotrophic marker, LEU2, used to disrupt the endochitinase gene.

DETAILED DESCRIPTION OF THE INVENTION

Figure 1:
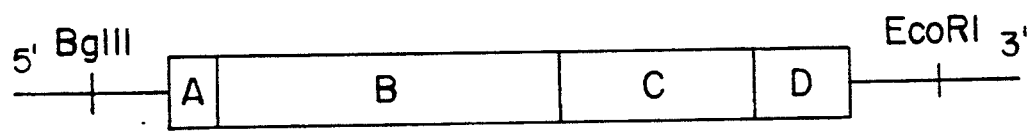
FIG. 1 is a schematic representation of the yeast endochitinase gene, CTS2.

The present invention is based on the cloning and sequencing of a gene, present in yeast, which encodes protein having endochitinase activity and on the demonstration that a carboxy-terminal portion of the protein encoded by the yeast gene is responsible for the observed high affinity binding of the protein to chitin. It has now been shown that a region of the *S. cerevisiae* endochitinase gene (designated D in FIG. 1) encodes the noncatalytic chitin-binding domain of the endochitinase. This gene portion has been linked to a gene encoding a Protein of interest, to produce a gene fusion construction. The gene fusion construction has been introduced into a host cell and expressed in that host, resulting in production of a recombinant or fusion protein which has chitin-binding activity and includes the protein of interest. The protein of interest has been shown to have retained its activity while bound to chitin.

The following is a detailed description of:

1) the yeast endochitinase gene shown to encode a product (protein/enzyme) which has an amino-terminal segment (designated B in FIG. 1) which catalyzes chitin hydrolysis and exhibits a low affinity for chitin and a carboxy-terminal segment (designated D in FIG. 1) which is a noncatalytic chitin-binding domain responsible for the observed high affinity binding of the enzyme to chitin;

2) gene fusion constructions which include: a) all of the region of the endochitinase gene encoding chitin-binding activity or a portion of that region (i.e., a portion sufficient to encode a product capable of binding ehitin); b) a gene of interest; and, optionally, c) other nucleotide sequences or genes useful for expression and/or secretion of the encoded chitin-binding activity and the protein of interest;

3) recombinant or fusion proteins encoded by the gene fusion constructions;

4) a method of making the gene fusion constructions and expressing them in appropriate host cells-to produce fusion proteins; and 5) a method of immobilizing and/or purifying a protein of interest by producing it as a component of a fusion protein which binds to chitin.

The description which follows refers to the *S. cerevisiae* endochitinase gene and fusion proteins in which one component is the chitin-binding domain of endochitinase. It is to be understood, however, that other genes or gene portions (e.g., from a yeast strain other than *S. cerevisiae* or from other organisms in which similar activity occurs) can be used in a similar manner to produce gene fusion constructions encoding fusion proteins which bind chitin (or an equivalent material in another organism) and contain the protein encoded by a gene of interest.

The present invention is meant to include functional equivalents or derivatives of the sequence of the gene fusion construction which encode the same amino acid sequence of the chitin-binding domain and the protein of interest. The term "functional equivalents or derivatives" is meant to include the fragments, variants, or analogs of the nucleotide sequences which encode a protein having the same properties and biological effect as the claimed protein. A "fragment" of a molecule, such as the nucleotide sequences or polypeptides of the present invention, is meant to refer to a subset of the molecule. A "variant" or "analog" of such molecule is meant to refer to a molecule substantially similar to the entire molecule or a fragment thereof.

A molecule is said to be "substantially similar" to another molecule if the nucleotide sequence or amino acid sequence of both molecules is substantially the same, and if both molecules possess a similar biological activity.

S. cerevisiae endochitinase gene

*Saccharomyces cerevisiae* contains an endochitinase activity which degrades chitin. The enzyme is normally secreted into the culture media of actively growing cells and can be purified in a single step by affinity adsorption to its substrate. The endochitinase gene, CTS2, has been cloned and sequenced. The nucleotide sequence of CTS2 is shown in FIG. 2. DNA deletion analysis and proteolysis experiments have demonstrated that a portion of the protein located at the carboxy-terminus is responsible for the observed high affinity binding of the enzyme to chitin (FIG. 1). The amino-terminal segment (shown as Region B in FIG. 1) catalyzes chitin hydrolysis and exhibits a low affinity toward the substrate. The present invention covers the use of the noncatalytic chitin binding domain (shown as Region D on Scheme 1) of chitinase, such as yeast endochitinase, in gene fusion constructs to impart chitin binding to proteins. The *S. cerevisiae* endochitinase gene, designated CTS2, has been cloned and sequenced; the location and the nucleotide sequence of each region indicated in FIG. 1 are indicated in FIG. 2, along with the corresponding amino acid sequence for each. The region designated A in FIG. 1 is the signal sequence of CTS2 and participates in secretion of endochitinase from yeast cells into culture media. The location of the signal sequence is shown in FIG. 2. Inclusion of the endochitinase signal sequence (or of another appropriate signal sequence) in the fusion protein of the present invention results in secretion of the fusion protein into culture media. The chitin-binding domain of endochitinase is represented in FIG. 2. The entire chitin-binding domain or a portion of the domain sufficient to exhibit chitin-binding activity can be included in the fusion protein of the present invention. Alternatively, the amino acid sequence of the naturally-occurring endochitinase chitin-binding domain (e.g., from *S. cerevisiae*) can be modified (e.g., by substitutions, additions and/or deletions of one or more amino acids) in such a way that chitin-binding ability of the modified domain is altered (generally, enhanced).

Gene Fusion Constructions Encoding a Fusion Protein Containing a Yeast Endochitinase Chitin-Binding Region and a Protein of Interest According to the present invention, a gene fusion construction encoding a protein of interest (e.g., a protein or polypeptide to be expressed and immobilized and/or purified by the present invention) and the chitinase chitin-binding domain is produced, using known techniques. The construct is prepared by joining a nucleotide sequence encoding the protein of interest and a second nucleotide sequence encoding all or a portion of the chitinase chitin-binding peptide. The two components of the gene fusion construction will generally be adjacent to one another (i.e., with few or no intervening nucleotides), but can also be separated by nucleotides, provided that the resulting fusion protein (which will have amino acid(s) between the chitin-binding domain and the protein of interest) retains both properties (i.e., chitin-binding and the amino acid sequence of the protein of interest).

Optionally, a signal sequence can also be included in the gene fusion construction. The signal sequence can be that of the endochitinase (as described herein, *S. cerevisiae* endochitinase) or can be from a different source. Further, a promoter, from which expression of the gene fusion construction is controlled, can also be included in the construction or can be present in the expression vector into which the construction is inserted. The promoter can be a yeast promoter, such as the endochitinase promoter, or a promoter of non yeast origin.

In one embodiment of the present invention, the *S. cerevisiae* endochitinase signal sequence and chitin-binding sequence and flanking sequences are cleaved from the endochitinase gene, and DNA encoding the gene of interest is inserted downstream of the signal sequence and upstream of the chitin binding sequence, as represented in FIG. 3. Inclusion of a signal sequence in the gene fusion construction results in a fusion protein which will be secreted into culture media. The signal sequence directs the passage of the protein through the cell membrane. Such signal or "pre" sequences are characteristic of secreted proteins and consist mainly of hydrophobic amino acid residues which determine the "export" of the protein across the cell membranes. The chitinase signal sequence can be incorporated into a vector with the gene of interest and the gene encoding the chitin binding domain with appropriate flanking and promoter sequences. Generally, the signal sequence is located upstream of the gene to be secreted. If it is not intended that the fusion protein be secreted into culture media, a signal sequence is not included in the gene fusion construction. In this case, the fusion protein will be recovered from the host cells themselves, after disruption of the cells (e.g., mechanically).

Where the nucleotide sequence of any component(s) of the gene fusion construction (e.g., the gene of interest, chitinase chitin-binding sequence, signal sequence, promoter) is known, the respective nucleotide sequences can be synthesized by known methods of nucleotide synthesis (e.g., the phosphate triester method). Alternatively, the nucleotide sequences can be obtained from naturally occurring sources (e.g., by isolating and cloning them) using known techniques.

The *S. cerevisiae* gene encoding endochitinase enzyme has been isolated and cloned, as described in the Exemplification. Thus, it is possible to use techniques described herein to isolate and clone the gene and obtain the necessary domain encoding chitin-binding activity. Alternatively, a nucleotide sequence having all or a portion of the nucleotide sequence of domain D represented in FIG. 2 can be produced chemically or mechanically. This is also the case for the endochitinase signal sequence and/or promoter.

As described in the Exemplification, a gene fusion construction which includes the *S. cerevisiae* endochitinase signal sequence and gene segment encoding chitin-binding activity, a gene encoding invertase activity (Kaiser et al., 1987, *Science*, 235: 312-317) and flanking sequences (in this case, the promoter and TATA elements located upstream of the endochitinase signal sequence) has been produced, incorporated into an expression vector and introduced into (expressed in) an appropriate host.

As described in the Exemplification, a nucleotide sequence encoding the endochitinase enzyme was cloned in yeast. The polynucleotide was cleaved by restriction enzymes, at the sites shown in FIG. 3, to yield the signal sequence and chitin binding domain, and including flanking sequences. The signal sequence and chitin-binding domain sequence were linked to the invertase gene, to produce a gene fusion construction (FIG. 3).

Cloning and Expression Vectors

Figure 4:
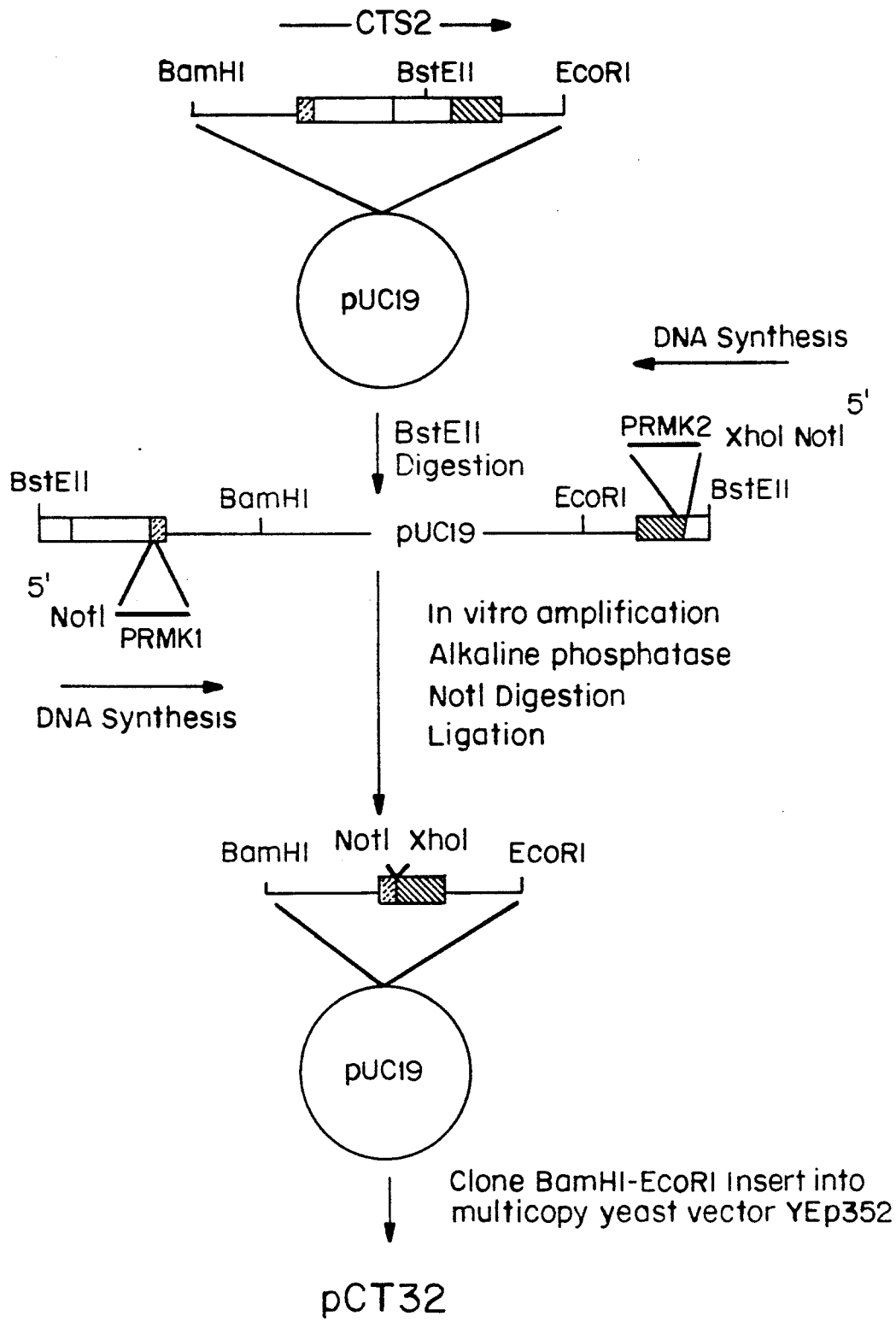
FIG. 4 is a schematic representation showing construction of the expression vector, pCT32, used for expression of gene fusion construction in yeast.
Figure 5:
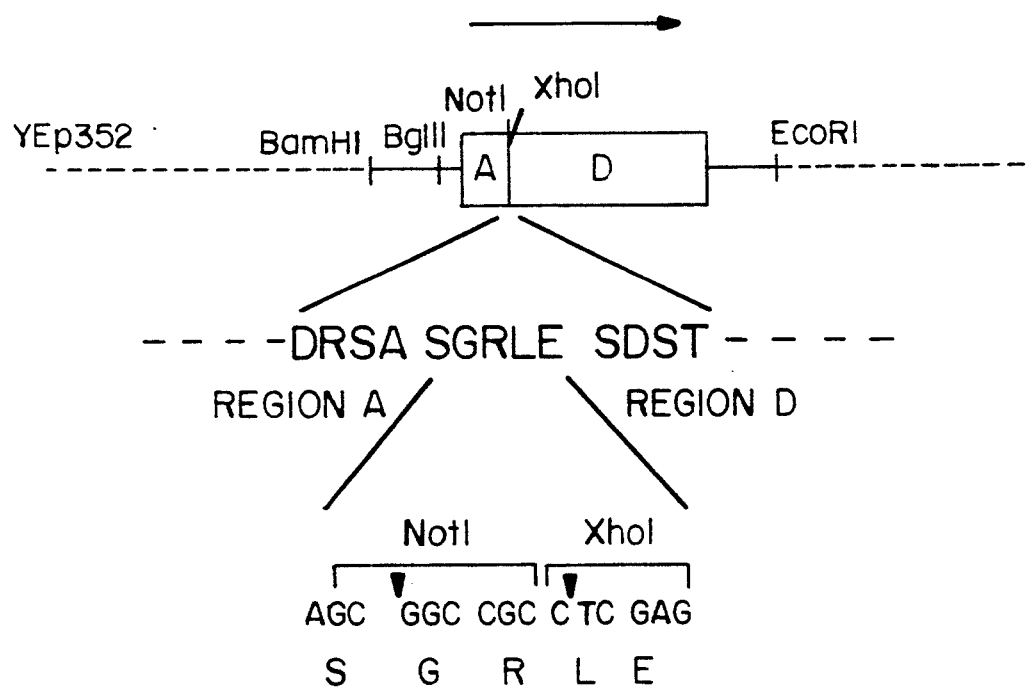
FIG. 5 shows sequence details of the expression vector pCT32.

The gene fusion construction of the present invention (i.e., one including a sequence encoding a chitin-binding product and a protein of interest, as well as, optionally, a signal sequence and a promoter sequence) is incorporated into an appropriate vector for introduction into a host cell for expression of the gene. In one embodiment of the present invention, the gene fusion construction encoding the *S. cerevisiae* endochitinase promoter, signal peptide and chitin-binding domain and a protein of interest (invertase) was incorporated into the multicopy yeast vector, YEp352. (Hill et al., *Yeast*, 2:163-167 (1986)), in such a manner as to allow it to be expressed by the host cell along with the expression of the normal complement of proteins. Construction of such a vector, pCT32 (FIG. 1), is represented schematically in FIG. 4 and is described in detail in the Exemplification. Briefly, a 2.5 Kb BamHI-EcoR1 fragment containing the endochitinase gene, CTS2, was cloned into the *E. coli* vector pUC19. The plasmid vector was digested with BstE11, resulting in a cut within CTS2 coding sequences between the signal sequence and the chitin binding domain (FIG. 4). The resulting linearized plasmid served as a template for in vitro amplification of the DNA segment indicated. This resulted in precise deletion of regions B and C. Two unique restriction sites were introduced at the ends of the amplified fragment; when joined, they retained the reading frame between the two regions. (See the Exemplification). The deleted BamHI-EcoR1 inserts were cloned into the yeast/E. coli shuttle vector, YEp352, which was used to transform yeast strain MKY1315. One construction, designated pCT32, which reacted with antichitinase antibody, was used to make a gene fusion construction which, in addition to the *S. cerevisiae* endochitinase promoter, flanking sequences, signal sequence and chitin-binding domain, included an invertase gene. This construction, designated pCT33, was introduced into MKY1315, which was maintained under conditions appropriate for expression of the encoded fusion protein. (S ⓡe the Exemplification). The fusion protein was recovered from cell media by binding to chitin added to filtered culture supernatant. Results demonstrated (Exemplification and FIG. 7) that the fusion protein produced by the transformed cells exhibited chitin binding activity and invertase activity.

Application of the Present to Immobilization and/or Purification of a Protein of Interest It is possible, using the methods and gene fusion constructions as described herein, to produce and immobilize and/or purify any protein of interest as part of a fusion protein which has chitin-binding activity. A gene fusion construction useful for such a purpose will include a gene of interest and the endochitinase gene chitin-binding domain.

The gene of interest present in the construction is any gene or portion thereof not normally present in the endochitinase gene and can encode all or a portion of a protein or polypeptide of interest. It can also encode more than one protein or polypeptide or portion thereof. Any gene(s) or interest whose expression is desired can be incorporated into a gene fusion construction of the present invention.

The entire endochitinase gene region which encodes chitin binding activity or a portion of that region (i.e., a portion which encodes a product capable of binding chitin) can be included in the construction. The work described herein makes use of the *S. cerevisiae* endochitinase gene designated CTS2. A second *S. cerevisiae* endochitinase gene, designated CTS1, has also been isolated and cloned. Partial DNA sequence analysis shows that at the C-terminal ends, both genes show 98% conservation at the nucleotide level in the region of the chitin-binding domain (region D). At the protein level, the two demonstrate 100% homology in that region. All or a portion of the CTS1 chitin binding domain or all or a portion of a similar gene encoding chitin-binding protein from another yeast strain or other source can be used to produce gene fusion constructions.

Optional components of the gene fusion construction include a promoter, under the control of which expression of the gene of interest and endochitinase gene region occur, flanking sequences and a signal sequence. Such components can, as described herein, be obtained from *S. cerevisiae*. Alternatively, they can be from another source, such as another yeast strain, a bacterial cell or a mammalian cell.

Some or all of the components of the gene fusion construction can be obtained from sources in which they naturally occur (e.g., by extraction, isolation and cloning) or can be synthesized, using known techniques. The components can be immediately adjacent one another (i.e., with no intervening nucleotides) or can be separated by nucleotides not part of their sequence (e.g., a linker sequence), so long as the presence of such intervening nucleotides does not interfere with production of a fusion protein having chitin-binding activity and the amino acid sequence of the protein of interest.

The gene fusion construction is incorporated into an appropriate expression vector, such as pCT32, described herein.

In addition to containing the gene fusion construction, the vector can, optionally, contain a gene which encodes a selectable marker which will allow selection of recombinants containing the construction. The gene encoding the selectable marker can be placed under the control of the bacterial or chitinase promoter. Several types of marker genes can be used (e.g., LacZ).

After transfected cells have phenotypically expressed the presence of the gene, cells showing such expression are selected. A selected colony can then be used to seed a large scale culture.

The gene fusion construction is incorporated into the plasmid by known techniques, such as the use of restriction enzymes (to make cuts at points at which the construction will be inserted) followed by ligation. For example, the nucleic acid material is ligated using a ligase enzyme, such as T4 DNA ligase to produce the desired construct.

The vector is used to introduce the gene fusion construction into a host cell, where it will be expressed. Introduction can be accomplished, for example, by transfection, using calcium phosphate-facilitated transfection. (M. Wigler et al., *Cell* 14:725 (1978)). The host cell into which the gene fusion construction vector is introduced can be yeast, as described herein, or can be a mammalian cell or bacterial cell.

In one embodiment of the present invention, a plasmid vector is used to transfer the hybrid gene to a host yeast cell. Particularly useful for this purpose are yeast host cells which lack normal yeast endochitinase activity (See the Exemplification). In this case, all of the chitin binding activity of the transformed cell is attributable to the recombinant chitin-binding domain and subsequent recovery of chitin-binding protein will be "specific for" chitin-binding activity present in fusion proteins. As described in the Exemplification, a uracil auxotroph containing a disrupted CTS2 gene and, thus, lacking endochitinase activity, can be used for this purpose. The fusion protein is purified by addition of chitin to filtered culture media.

Fusion proteins can be liberated from chitin by treatment with 7M guanadine hydrochloride and potentially renatured by removal of the denaturant by dialysis or chromatography. One approach for the recovery of labile gene products in a soluble form is the introduction of unique protease cleavage sites between the gene of interest and the chitin-binding domain. Chemical or enzymatic treatment of the chitin conjugate would then liberate the desired peptide segment, leaving the chitin binding portion attached to chitin.

Using the herein described cloning and expression vectors and techniques, significant amounts of the fusion protein coded for by the gene fusion construction can be produced. Such proteins can be harvested from the culture medium and purified by binding to a chitin adsorbant.

This system has been used successfully to isolate an invertase (Suc2) chitin binding domain fusion protein. Further, the hybrid protein retained sucrose hydrolyzing activity while immobilized on chitin.

Uses of the Present Invention

The present invention can be used to immobilize and/or purify any protein (or proteins) of interest. It can be used, for example, to produce a protein or other gene product useful for therapeutic, preventive or diagnostic purposes (e.g., as a drug).

Binding of the fusion proteins to chitin is stable over a wide range of pH, salt, and many other common denaturants, making the isolated chitin-fusion conjugates useful as potential affinity matrices for the isolation of ligands or receptors. Also, catalytic surfaces generated by the immobilization of enzymes can be useful for the large scale production of their products.

The present invention will now be illustrated by the following exemplification, which is not to be taken as limiting in any way. .

Exemplification

The following example illustrates the invention and establishes that fusion of the chitin-binding domain sequences (region D shown in FIG. 1) to a gene of interest imparts novel chitin-binding affinity to the latter. In addition, the bound protein in this case was shown to have retained its catalytic properties, demonstrating the feasibility of immobilizing enzymes in an active form to chitin with this method. The specific example presented here is a fusion of the yeast invertase gene (SUC2) to the signal sequence and chitin binding domain of CTS2. Yeast invertase displays no inherent affinity towards chitin. The fusion, however, when expressed in an endochitinase minus yeast mutant, can be purified to homogeneity from culture media by affinity adsorption to chitin. The chitin-fusion protein conjugate, like the soluble fusion, will catalyze the hydrolysis of sucrose.

Preparation of Endochitinase-Minus Yeast Cells

Figures 6A, 6B:
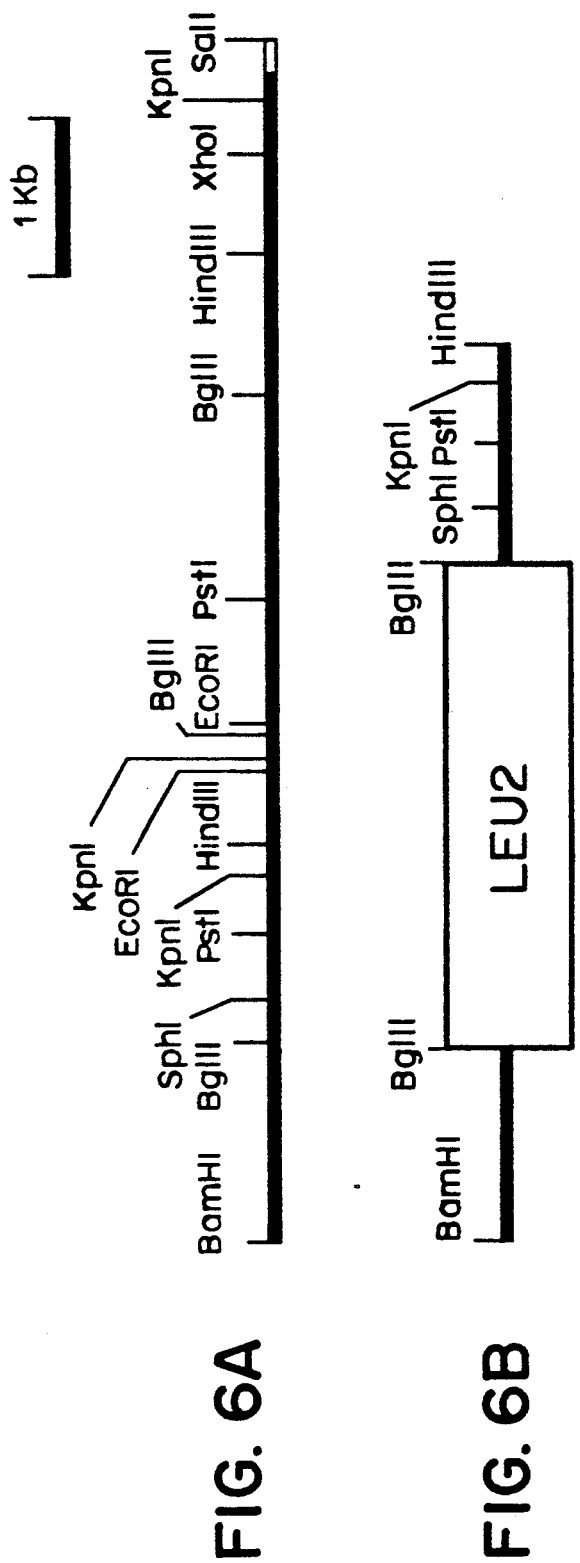
FIGS. 6A and 6B are schematic representations of the yeast endochitinase gene, CTS1.

An endochitinase minus mutant was produced by the single step disruption technique described by Rothstein (Rothstein, R. J. (1983), *Methods Enzymol.* 101: 202-211). The disruption utilized a 2.5 kb BamHI-HindIII fragment from pCT3, a subclone containing the structural gene for endochitinase, CTS1 (FIG. 6A). The auxotrophic marker, LEU2, was inserted at the unique BglII site indicated, which is located approximately 180 bp upstream from the endochitinase start codon (FIG. 6B). The haploid strain *S. cerevisiae* DBY1315 (MATαura3-52, lys 2-801, leu2-3, 112) was transformed with the disruption fragment shown in FIG. 6 and transformants were screened for endochitinase activity as described by Kuranda and Robbins. Kuranda, M. J. and P. W. Robbins, *Proc. Nat'l Acad. Sci. USA,* 84:2585-2589 (1987). The transformant, MKY1315 (MAT ,ura3-52, lys2-801, leu2-3, 112, cts2::LEU2), is an isolate from this screen which produced negligble levels of endochitinase activity. Analysis of genomic DNA isolated from MKY1315 by Southern blot analysis indicated integration had occurred within a region encoding a second homologous endochitinase gene designated CTS2. The second chitinase gene has subsequently been cloned by screening yeast genomic libraries introduced into MKY1315 and screening for transformants that restore endochitinase activity in the mutant. The entire CTS2 gene has been sequenced and subsequently used in constructions reported here (Sequence shown in FIG. 2). CTS1 has been partially sequenced. Both enzymes show similar chitin binding properties. Comparison of DNA sequences at the C-terminal ends of both genes show 98% conservation at the nucleotide level in the region of the chitin binding domain (region D), and 100% homology at the protein level.

Construction of Plasmid Vector, pCT32

The yeast expression vector pCT32 contains the signal sequence (region A, FIG. 1), and chitin binding domain (region D, FIG. 1) of CTS2 joined in frame and separated by the two unique restriction sites NotI and Xho. Transformation of MKY1315 with pCT32 results in secretion of region D in yeast, which can be recovered from culture media by binding a chitin. Insertion of the two unique restriction sites allows for introduction of new coding segments such that in frame fusions with region A and region D facilitate secretion in yeast and binding to chitin.

The construction of pCT32 is outline in FIG. 4. A 2.5 kb BamHI-EcoRI fragment containing CTS2 was cloned into the *E. coli* vector pUC19, yielding plasmid pCT30. The plasmid was digested with BstEII, which out within CTS2 coding sequences between the signal sequence and chitin binding domain. The linearized plasmid was used as a template for in vitro amplification of the indicated DNA segment, resulting in precise deletion of regions B and C. Restriction sites "tails" present on the ends of the primers were used to introduce two unique restriction sites at the ends of the amplified fragment which when joined retained the reading frame between the two regions. Conditions and reagents used in the amplification reaction are included in the GeneAmp DNA Amplification Reagent Kit (part #N001-0043/Perkin Elmer Cetus). Reactions were carried out in a Perkin Elmer Cetus DNA Thermal Cycler. The sequence of oligonucleotides used (PRMK1 and PRMK2) are given in the Table.

TABLE

SYNTHETIC OLIGONUCLEOTIDES USED IN FUSION EXPERIMENTS

PRIMER

PRMK1

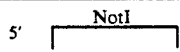

PRMK2

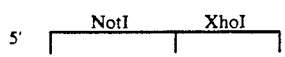

TABLE-continued
SYNTHETIC OLIGONUCLEOTIDES USED IN FUSION EXPERIMENTS

PRIMER

PRMK3  5'  —NotI—  3'
GGGCGGCCGCACAAACGAAACTAGCGATAGACCTTTGGTC

PRMK4  5'  —XhoI—  3'
GGCTCGAGTTTTACTTCCCTTACTTGGAACTTGTCAAT

The amplified product was ethanol precipitated and treated with alkaline phosphatase (calf intestine) to inhibit potential blunt end ligations. The digest was extracted with phenol/chloroform and ethanol precipated. The pellet was suspended in restriction buffer and then digested with NotI. The fragment was purified by electrophoresis on low melting point agarose, excised and ligated. Crouse, G. F. et al., *Methods Enzymol.* 101:202-211 (1983). Transformation of *E. coli* and restriction analysis of plasmids obtained from transformants by minipreparation indicated that the majority of the clones had deleted the desired region and had incorporated the anticipated Not1 and Xho1 sites. The deleted BamHI-EcoRI inserts isolated from several independent transformants were cloned individually into the polylinker region of the yeast/*E. coli* shuttle vector YEp352. Hill, J. E. et al., *Yeast*, 2:163-167 (1986). The resulting set of constructions were used to transform yeast strain MKY1315. Yeast cell lysates from individual transformants were screened by Western blot analysis with antichitinase antibody for the production of the truncated CTS2 gene product. Two of the three constructions analyzed produced an immunologically active product of the expected size. One of these (designated pCT32) was chosen for the fusion experiments described below.

Construction of Plasmid Vector pCT33 (SUC2-Chitin-Binding Domain Fusion)

A precise segment of the yeast invertase coding sequences with Not1 and Xho1 cohesive ends was produced by in vitro DNA amplification, as described above. The SUC2-containing plasmid, pRB576 (Kaiser, C. A. et al., (1987) *Science*, 235:312-317) was linearized with EcoRI which cut outside SUC2 coding sequences and used as a template. The primers used (PRMK3 and PRMK4) are shown in the Table. The region of amplification (1.5kb) deletes the first 2 amino acids of the secreted message and extends to and includes the last amino amino acids of the coding sequence. Taussig, R. and M. Carlson, *Nucl. Acid Res.*, 11:1943-1954. Secretion of the protein is therefore dependent on utilization of the signal sequence of CTS2. The DNA was concentrated from the amplification reaction by ethanol precipation. The pellet was then suspended in restriction buffer and simultaneously digested with NotI and XhoI. The invertase fragment was purified by electrophoresis in low melting point agarose and ligated with pCT32 which had been similarly digested and purified. *E. coli* transformants were screened for incorporation of insert by restriction analysis of plasmid DNA isolated by minipreparation. Five clones containing inserts were transformed into MKY1315 yeast cells. Four contained invertase activity and produced a protein product which reacted with both antiinvertase and antichitinase antibodies on Western blots. One of these was chosen for further analysis and designated pCT33. A deposit of pCT33 has been made at the American Type Culture Collection (Rookville, MD) under terms of the Budapest Treaty; deposit number 20924 has been assigned to the deposit.

Isolation of Fusion Proteins from Culture Media by Chitin Binding

Figure 7:
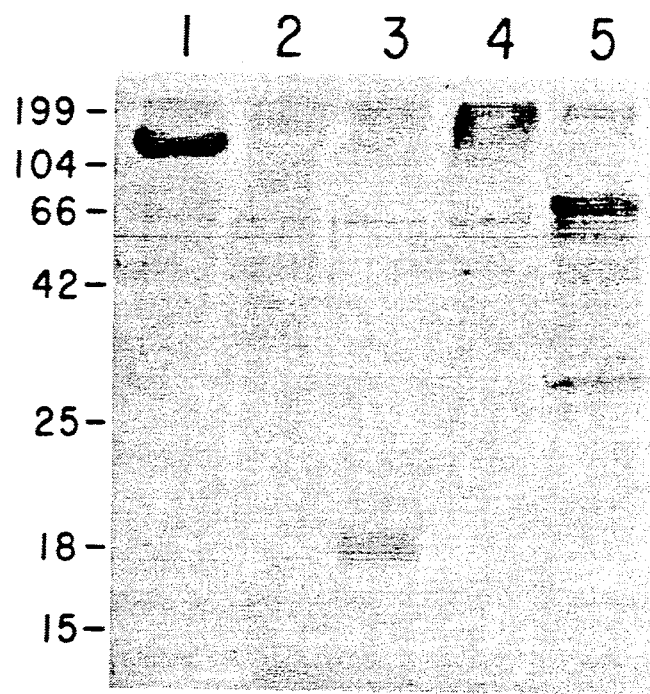
FIG. 7 shows chitin-bound proteins isolated from yeast culture supernatants, by SDS gel electrophoresis: Lane 1: endochitinase from *S. cerevisiae* DBY1315 which produces wild-type levels of endochitinase; Lane 2: no protein from *S. cerevisiae* MKY1315/YEp352 endochitinase minus mutant; Lane 3: *S. cerevisiae* MKY1315/pCT32, which expresses the chitin-binding domain of CTS32; Lane 4: *S. cerevisiae* MK1315/pCT33 which expresses the invertase-chitin binding domain fusion protein; and Lane 5: the protein in Lane 4 treated with EndoH.

Cultures of MKY1315 containing fusion plasmids were initially grow overnight in 10 mls of SD medium supplemented with lysine at 30 C. The cultures were diluted into 500 mls YPD medium and allowed to grow for an additional 16 hours after which time the cells were pelleted and the supernatant was collected. The media was then filtered through Millipore-Type HA membrane (0.45 micrometer). Chitin used in binding experiments was prepared from purified chitin (Sigma) which had been boiled in 1% SDS/1% beta-mercaptoethanol and then extensively washed with water. 0.5 mls of chitin (wet) was added per 500 mls of filtered culture supernatant. The suspension was swirled overnight on a rotary shaker at 4° C. The chitin was then collected by filtration using a Type HA membrane and washed with 500mls of solution A (0.8%NaCl, 0.02%KCl, 0.12%Na2HPO4, 0.02%KHPO4). A small volume of Solution A was added to the surface of the membrane and the chitin was suspended with the aid of a Pasteur pipet. The suspension was transferred to 12 ml Disposable Poly-Pep column (Bio-Rad) and the column was drained of excess buffer. Chitin-fusion protein conjugates were then stored in columns under a small volume of Solution A at 4 C. 50 microliter samples of chitin were suspended in 100 microliter of 2%SDS, 5% beta-mercaptoethanol, 10% glycerol and heated to 100° C. for 10 minutes. The samples were centrifuged and the supernatants analyzed by SDS gel electrophoresis (FIG. 7). Transformation of MKY1315 results in the secretion of a 18 kd peptide which binds to chitin. The size is identical to the peptide obtained by partial proteolysis of CTS2 originally used to define the chitin binding domain. Direct analysis of the chitin bound fusion produced by pCT33 shows a single heterogeneous band of high molecular weight (FIG. 7, lane 4) typical of glycosylated invertase. Treatment with endo-beta-D-acetylglucosaminidase H yields a single polypeptide (70 kd) consistent with anticipated molecular weight of the fusion (64 kd). 1.2 mg of invertase-fusion protein can be purified per liter of culture supernatant using the above technique. Approximately 80% of the soluble activity is recovered in the form of an insoluble chitin conjugate, resulting in a net 8000-fold purification as compared to the specific activity of the starting culture media.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

I claim:

1. Isolated DNA consisting essentially of DNA encoding the noncatalytic chitin-binding domain of yeast endochitinase.

2. Isolated DNA consisting essentially of DNA encoding the noncatalytic chitin-binding domain of yeast endochitinase having all or a portion of the nucleotide sequence of the CTS2 gene chitin binding domain as represented in FIG. 2.

3. Isolated DNA of claim 2 additionally comprising DNA encoding the signal sequence of yeast endochitinase.

4. Isolated DNA encoding the noncatalytic chitin-binding domain of yeast endochitinase and having all or a portion of the nucleotide sequence encoding the non-catalytic chitinbinding domain of the CTS2 gene as represented in FIG. 2 and the signal sequence of yeast endochitinase wherein the DNA encoding the noncatalytic chitin-binding domain of yeast endochitinase and the DNA encoding the signal sequence of yeast endochitinase are joined in frame and separated by the two unique restriction sites Not1 and Xho1.

5. A gene fusion construction comprising:
   a. a nucleotide sequence consisting essentially of DNA encoding the non-catalytic chitin-binding domain of yeast endochitinase; and
   b. a gene of interest.

6. A gene fusion construction of claim 5, wherein the yeast endochitinase is from *Saccharomyces cerevisiae*.

7. A gene fusion construction of claim 6, wherein the gene of interest is the invertase gene.

8. A gene fusion construction of claim 5 additionally comprising DNA consisting essentially of the signal sequence of yeast endochitinase and the yeast endochitinase promoter.

9. A plasmid comprising the nucleotide sequence of claim 2.

10. A plasmid containing the DNA of claim 3.

11. The plasmid pCT32.

12. A plasmid of claim 10, further comprising a gene of interest.

13. The plasmid pCT33.

14. A host cell transformed by plasmid pCT32.

15. A host cell of claim 14, which is *Saccharomyces cerevisiae*.

16. A host cell transformed by plasmid pCT33.

17. A plasmid vector comprising a gene fusion construction encoding a fusion protein, said fusion protein consisting essentially of a yeast endochitinase signal sequence, a protein of interest and the noncatalytic chitin-binding domain of a yeast endochitinase.

18. A plasmid vector of claim 17, wherein the protein of interest is invertase.

19. A host cell transformed by the plasmid vector of claim 18.

20. A host cell of claim 19 which is *Saccharomyces cerevisiae*.

21. A fusion protein produced by the transformed host cell of claim 20.

22. A fusion protein comprising a protein of interest and a chitin-binding protein, wherein the fusion protein is expressed by a gene fusion construction comprising:
   a) a nucleotide sequence consisting essentially of DNA encoding the non-catalytic chitin-binding domain of yeast endochitinase; and
   b) a gene interest.

23. A fusion protein of claim 22, in which the protein of interest is invertase.

24. A method of purifying a selected fusion protein from cell culture medium of transformed cells expressing the fusion protein, comprising the steps of:
   a. introducing into appropriate host cells a gene fusion construction, the gene fusion construction comprising:
      i) a nucleotide sequence consisting essentially of DNA encoding the noncatalytic chitin-binding domain of yeast endochitinase;
      ii) a gene of interest encoding a protein of interest; and
      iii) a signal sequence; and
   b. maintaining host cells containing the gene fusion construction in medium and under conditions appropriate for expression of the fusion protein and secretion of the fusion protein into the medium;
   c. contacting medium with chitin under conditions appropriate for binding of the portion of the fusion protein capable of binding chitin and chitin to occur; thereby producing medium containing fusion protein bound to chitin; and
   d. separating the fusion protein bound to chitin from the medium and dissociating the fusion protein bound to chitin from the chitin.

25. A method of claim 24, wherein the protein of interest is invertase and the yeast endochitinase is *Saccharomyces cerevisiae* endochitinase.

26. A method of claim 24, wherein the host cells are *Saccharomyces cerevisiae*.

27. A method of claim 24, further comprising the step of treating the fusion protein in step (d) under conditions appropriate to remove the non-catalytic chitin-binding domain of yeast endochitinase from the protein of interest to obtain free, biologically active protein of interest.

28. Isolated DNA encoding essentially the noncatalytic chitin-binding domain of yeast endochitinase and the signal sequence of yeast endochitinase wherein the DNA encoding the noncatalytic chitin-binding domain of yeast endochitinase and the DNA encoding the signal sequence of yeast endochitinase are joined in frame and separated by the two unique restriction sites Not1 and Xho1.

* * * * *